United States Patent [19]

Sequeira et al.

[11] Patent Number: 4,499,108

[45] Date of Patent: Feb. 12, 1985

[54] STABLE PLEASANT-TASTING ALBUTEROL SULFATE PHARMACEUTICAL FORMULATIONS

[75] Inventors: Joel A. Sequeira, New York, N.Y.; Michael A. Zupon, Madison, N.J.

[73] Assignee: Schering Corporation, Madison, N.J.

[21] Appl. No.: 502,427

[22] Filed: Jun. 8, 1983

[51] Int. Cl.³ .............................................. A61K 31/135
[52] U.S. Cl. .................... 514/653; 514/574; 514/568
[58] Field of Search ................ 424/330, 315

[56] References Cited

U.S. PATENT DOCUMENTS

| | | | |
|---|---|---|---|
| 3,485,915 | 12/1969 | Gerstein | 424/81 |
| 3,705,233 | 12/1972 | Lunts et al. | 424/45 |
| 4,034,087 | 7/1977 | Voorhees | 424/317 |
| 4,251,534 | 2/1981 | Aldrich et al. | 424/244 |

OTHER PUBLICATIONS

Hakes et al., J. Pharm. Pharmol., 32 Suppl. 49P, (1980).
Remington's Pharmaceutical Sciences, 16th Ed.; (1980), p. 1245.
The Merck Index, 9th Ed.; (1976), "Albuterol", p. 30.

*Primary Examiner*—Leonard Schenkman
*Assistant Examiner*—Joseph A. Lipovsky
*Attorney, Agent, or Firm*—Stephen I. Miller

[57] ABSTRACT

Albuterol sulfate syrups that are pleasant-tasting and stable upon prolonged storage.

6 Claims, No Drawings

STABLE PLEASANT-TASTING ALBUTEROL SULFATE PHARMACEUTICAL FORMULATIONS

This invention provides a pleasant-tasting, highly-stable albuterol sulfate syrup.

Albuterol sulfate, which has the formula

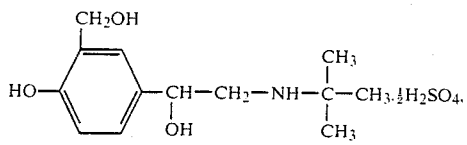

is a beta-adrenergic antagonist and is indicated for the relief of bronchospasm. The compound is described in U.S. Pat. No. 3,705,233. For maximum stability it is known that aqueous solutions of the compound should contain buffer to control the pH to between 2 and 5. Such buffered solutions are not pleasant tasting unless they contain a sweetener.

Ordinary sugars such as glucose and fructose are known to degrade albuterol sulfate, see, for example Hakes et al., J. Pharm Pharmol. 32, Suppl. 49P, (1980). Even a plain buffered albuterol sulfate solution, i.e. one containing no sugar or other ingredients, degrades upon prolonged storage.

SUMMARY OF THE INVENTION

We have unexpectedly discovered specific formulations that provide a pleasant-tasting albuterol sulfate syrup that is even more stable than a plain buffered solution. The present invention comprises a stable, pleasant-tasting pharmaceutical formulation comprising per ml of the formulation:

(a) 0.2 to 6.0 mg albuterol sulfate,
(b) sufficient buffer to control the pH of the formulation to 2 to 5,
(c) sufficient preservative to prevent microbial growth,
(d) 0.1 to 2.0 mg saccharin,
(e) sufficient viscosity imparting agent to cause the viscosity of the formulation to be higher than that of water at room temperature, and
(f) water q.s. for 1 ml.

DETAILED DESCRIPTION OF THE INVENTION

Syrups in accordance with the invention contain albuterol sulfate in the amount of from 0.2 to 6.0 mg/ml of syrup, more preferably 0.45 to 0.55 mg/ml.

THe syrups are buffered to control the pH to 2 to 5, more preferably 3 to 4.5. The preferred buffer is a combination of citric acid and sodium citrate dihydrate in accordance with the following table.

|  | Amount, mg/ml of syrup | |
| --- | --- | --- |
|  | Broad | Preferred |
| citric acid | 1.4 to 11.2 | 2.5 to 3.5 |
| sodium citrate dihydrate | 0.8 to 6.4 | 1.3 to 2.3 |

The syrups contain sufficient preservative to prevent microbial growth. The preferred preservative is sodium benzoate in the amount of 0.5 to 3 mg/ml of syrup, more preferably 0.5 to 1.5 mg/ml. Other preservatives such as parabens are also acceptable.

To render the syrups pleasant-tasting, saccharin in the amount of 0.1 to 2.0 mg/ml of syrup, more preferably 0.2 to 0.4 mg/ml, are added.

A viscosity imparting agent is in the formulation to cause the viscosity to be higher than that of water at room temperature and thus render it less likely to spill when administered by spoon, as is customary. The preferred thickening agent is hydroxypropyl methyl cellulose in the amount of 2 to 8 mg/ml of syrup, more preferably 4 to 5 mg/ml. Other thickening agents such as hydroxyethyl cellulose and methyl cellulose are acceptable.

Optional ingredients include a coloring agent to impart a pleasant color and flavoring to impart a pleasant flavor, thus improving the organoleptic properties of the syrup.

Water is present as the major component to adjust the syrup to desired volume.

EXAMPLE

A syrup is prepared with the following ingredients.

| Ingredient | Amount, per ml of syrup |
| --- | --- |
| albuterol sulphate | 0.482 mg |
| citric acid, anhydrous | 2.8 mg |
| sodium citrate, dihydrate | 1.59 mg |
| sodium benzoate | 1 mg |
| saccharin | 0.2 mg |
| hydroxypropyl methylcellulose | 4.5 mg |
| coloring agent[1] | 0.015 mg |
| flavor[2] | 0.0005 ml |
| water | q.s. ad 1 ml |

[1] FD & C Yellow No. 6
[2] Strawberry, Artifical

Heat about 95% of the purified water to about 85° C. Add the hydroxypropyl methylcellulose to the water and mix. Cool the solution to about 55° C. while mixing. Add the saccharin, citric acid, sodium citrate dihydrate, sodium benzoate, and albuterol sulfate to the solution. Mix until dissolved while cooling to about 30° C. Dissolve the coloring agent in a second portion of the purified water and add this solution to the previous solution. Mix until homogeneous. Add the flavor to the solution and mix. Adjust the volume of the solution with the remainder of the purified water and mix until the solution is homogeneous.

Syrups made in accordance with the example were tested for stability at various temperatures with the following results.

| Storage Time (months) | Temperature, (°C.) | Weight Percent of Albuterol Sulfate Remaining |
| --- | --- | --- |
| 1 | Room Temp. | 100 |
|  | 35 | 100 |
|  | 45 | 100 |
|  | 55 | 100 |
| 2 | Room Temp. | 100 |
|  | 35 | 100 |
|  | 45 | 100 |
|  | 55 | 98 |
| 3 | Room Temp. | 100 |
|  | 35 | 100 |
|  | 45 | 102 |
|  | 55 | 100 |

These results indicate that syrups in accordance with the example will have a shelf life of at least three years when stored at 2° to 30° C., well in excess of the shelf life of syrups containing sugar. Surprisingly, the stability of our syrups is even better than that of plain buffered albuterol sulfate aqueous solutions.

What is claimed is:

1. A stable, pleasant-tasting pharmaceutical formulation comprising per ml of the formulation:
   (a) 0.2 to 6.0 mg albuterol sulfate,
   (b) sufficient buffer to control the pH of the formulation to 2 to 5,
   (c) sufficient preservative to prevent microbial growth,
   (d) 0.1 to 2.0 mg saccharin,
   (e) sufficient viscosity imparting agent to cause the viscosity of the formulation to be higher than that of water at room temperature, and
   (f) water q.s. for 1 ml.

2. The formulation of claim 1 wherein elements (b), (c), and (e) comprise per ml of the formulation:
   (b) 1.4 to 11.2 mg citric acid and 0.8 to 6.4 mg sodium citrate dihydrate,
   (c) 0.5 to 3 mg sodium benzoate,
   (e) 2 to 8 mg hydroxypropyl methyl cellulose.

3. The formulation of claim 2 comprising per ml of the formulation:
   (a) 0.45 to 0.55 mg albuterol sulfate,
   (b) 2.5 to 3.5 mg citric acid and 1.3 to 2.3 mg sodium citrate dihydrate,
   (c) 0.5 to 1.5 mg sodium benzoate,
   (d) 0.1 to 0.4 mg saccharin,
   (e) 4 to 5 mg hydroxypropyl methylcellulose, and
   (f) water q.s. for 1 ml.

4. The formulation of claim 3 comprising per ml of the formulation:
   (a) 0.482 mg albuterol sulfate,
   (b) 2.8 mg citric acid and 1.59 mg sodium citrate,
   (c) 1 mg sodium benzoate,
   (d) 0.2 mg saccharin,
   (e) 4.5 mg hydroxypropyl methylcellulose,
   (f) water q.s. for 1 ml,
   (g) sufficient coloring agent to impart a pleasant color, and
   (h) sufficient flavor to a impart a pleasant flavor.

5. The formulation of claim 4 wherein said coloring agent is FD&C Yellow No. 6, and said flavor is artificial strawberry flavor.

6. The formulation of claim 5 wherein the amount of FD&C Yellow No. 6 is 0.015 mg/ml of the formulation and the about of artifical strawberry flavor is 0.0005 ml/ml of the formulation.

* * * * *